United States Patent [19]
Hmelar et al.

[11] Patent Number: 5,772,657
[45] Date of Patent: Jun. 30, 1998

[54] SIDE FIRING FIBER OPTIC LASER PROBE

[75] Inventors: Michael Hmelar, Palo Alto; Nubar Manoukian, Cupertino, both of Calif.

[73] Assignee: Coherent, Inc., Santa Clara, Calif.

[21] Appl. No.: 781,933

[22] Filed: Jan. 8, 1997

Related U.S. Application Data

[63] Continuation of Ser. No. 427,173, Apr. 24, 1995, abandoned.

[51] Int. Cl.⁶ .................................................. A61B 17/36
[52] U.S. Cl. .............................. 606/15; 606/13; 606/14; 606/17
[58] Field of Search .................... 606/13–18, 7; 607/88, 89

[56] References Cited

U.S. PATENT DOCUMENTS

| | | | |
|---|---|---|---|
| 4,445,892 | 5/1984 | Hussein et al. | 604/101 |
| 4,648,892 | 3/1987 | Kittrell et al. | 65/4.21 |
| 4,672,961 | 6/1987 | Davies | 128/303.1 |
| 4,740,047 | 4/1988 | Abe et al. | 350/96.15 |
| 5,129,895 | 7/1992 | Vassiliadis et al. | 606/6 |
| 5,242,438 | 9/1993 | Saadatmanesh et al. | 606/15 |
| 5,248,311 | 9/1993 | Black et al. | 606/15 |
| 5,253,312 | 10/1993 | Payne et al. | 385/31 |
| 5,254,114 | 10/1993 | Reed, Jr. et al. | 606/15 |
| 5,257,991 | 11/1993 | Fletcher et al. | 606/15 X |
| 5,366,456 | 11/1994 | Rink et al. | 606/15 X |
| 5,370,649 | 12/1994 | Gardetto et al. | 606/17 |
| 5,428,699 | 6/1995 | Pon | 385/31 |
| 5,509,917 | 4/1996 | Cecchetti et al. | 606/15 |
| 5,537,499 | 7/1996 | Brekke | 385/31 |
| 5,562,657 | 10/1996 | Griffin | 606/17 |
| 5,571,099 | 11/1996 | Purcell, Jr. et al. | 606/17 |

FOREIGN PATENT DOCUMENTS

| | | | |
|---|---|---|---|
| 61-219904 | 9/1986 | Japan | G02B 6/10 |
| 3-63377 | 9/1991 | Japan | A61B 17/36 |
| WO 90/05562 | 5/1990 | WIPO | A61N 5/01 |

OTHER PUBLICATIONS

Advertising brochure from Endocare, a subsidiary or Cytocare, Inc., illustrating "ProLase™ II" and ProLase™ I (2–sided), one page.

*Primary Examiner*—John P. Lacyk
*Assistant Examiner*—Stephen Huang
*Attorney, Agent, or Firm*—Limbach & Limbach L.L.P.

[57] ABSTRACT

A side firing fiber optic probe is disclosed. The delivery end of the probe is provided with an angled face oriented to totally internally reflect the treatment beam out of the side surface of the fiber in a direction transverse to the longitudinal axis thereof. The delivery end of the probe is further configured to reduce secondary reflections which occur as the light strikes the side surface of the fiber. This result can be achieved by modifying the shape of the cladding material which surrounds the fiber core. In one approach, the ratio of the diameters of the clad to the core is increased. Other specific cladding configurations for reducing reflections can be used. In a further alternative, the surface of a glass capillary which surrounds the fiber can be optically coupled to the fiber. Each of these approaches functions to reduce unwanted light leakage from the fiber. In another aspect of the probe design, a stainless steel shield is provided which functions to protect the capillary and the fiber against cavitation effects which occur during use.

32 Claims, 12 Drawing Sheets

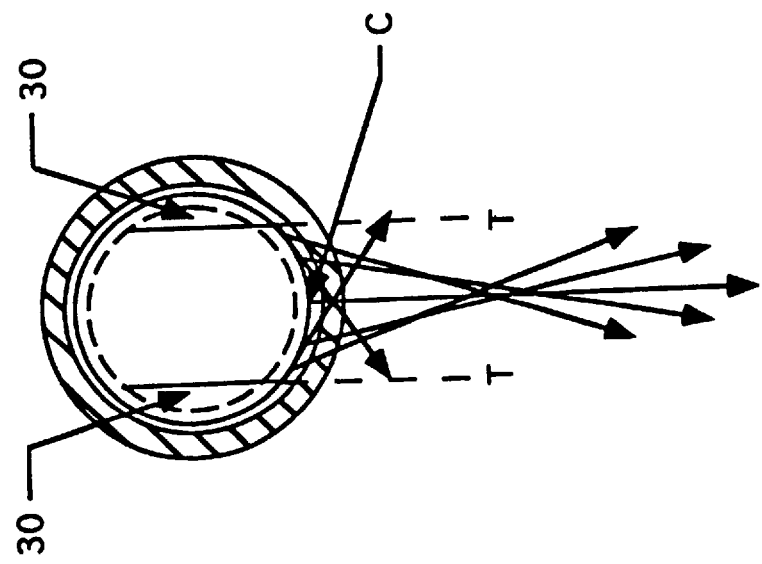
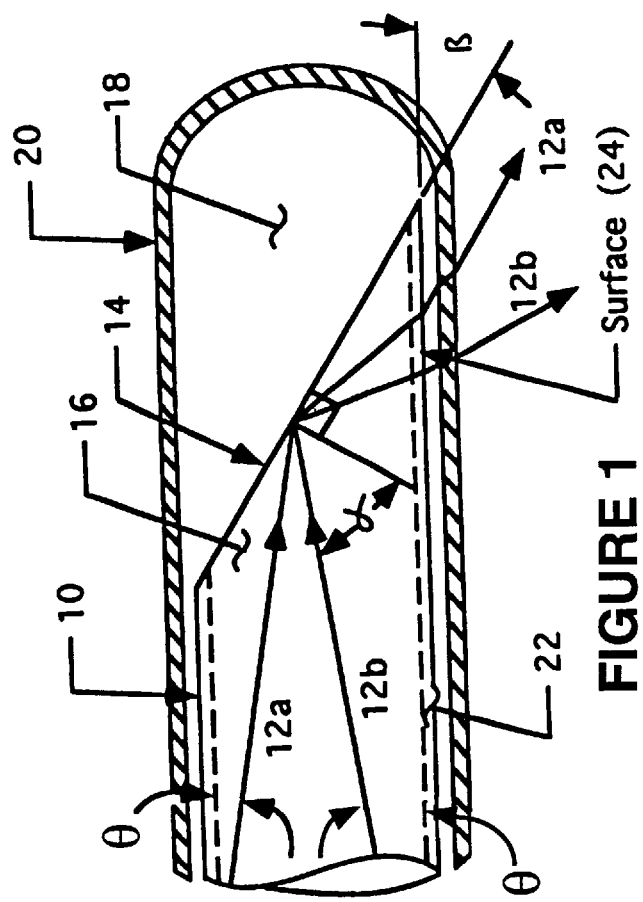
FIGURE 1
FIGURE 2a

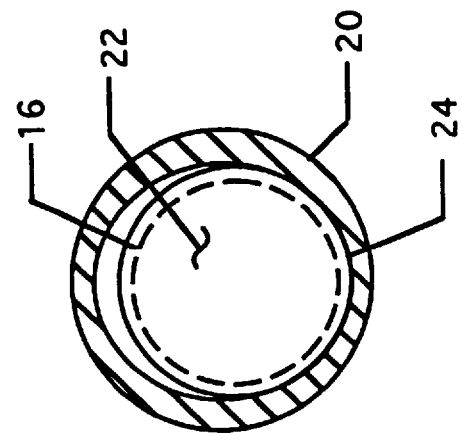
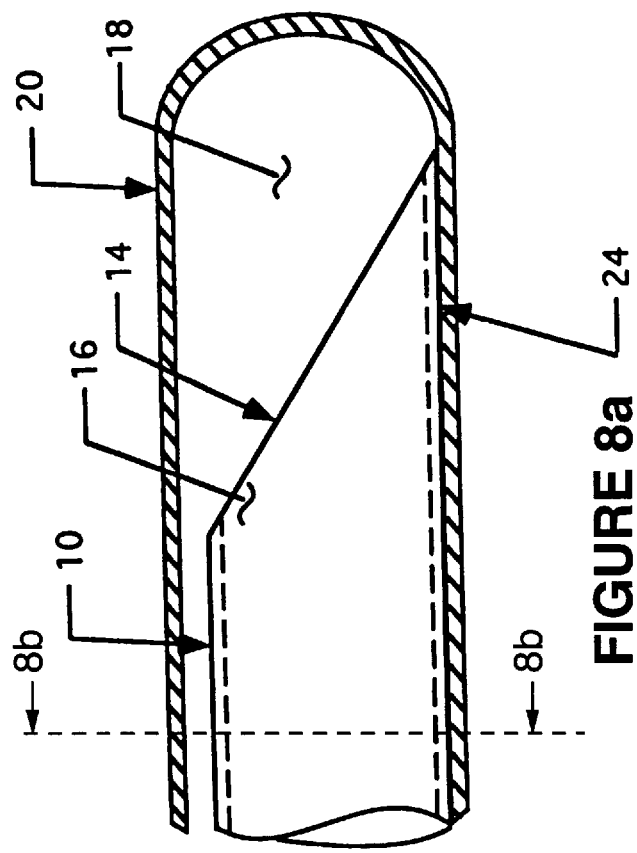
FIGURE 8b
FIGURE 8a

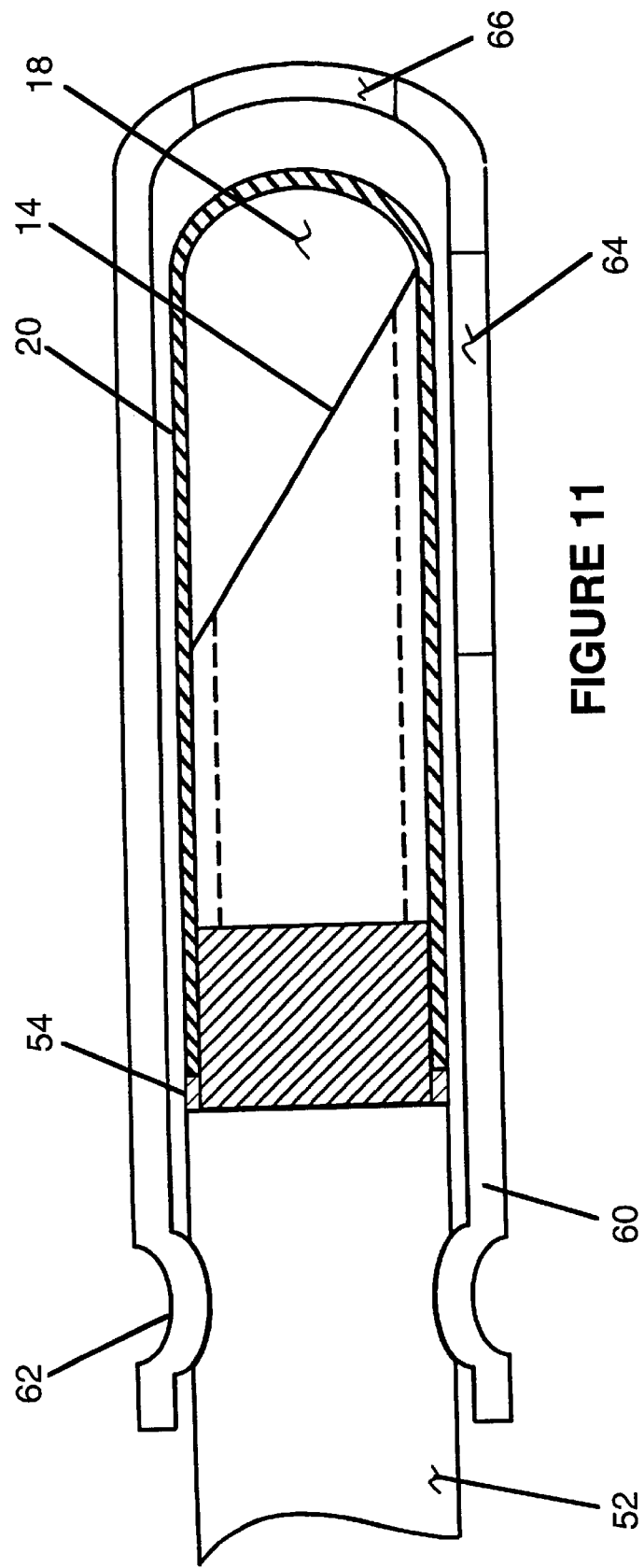

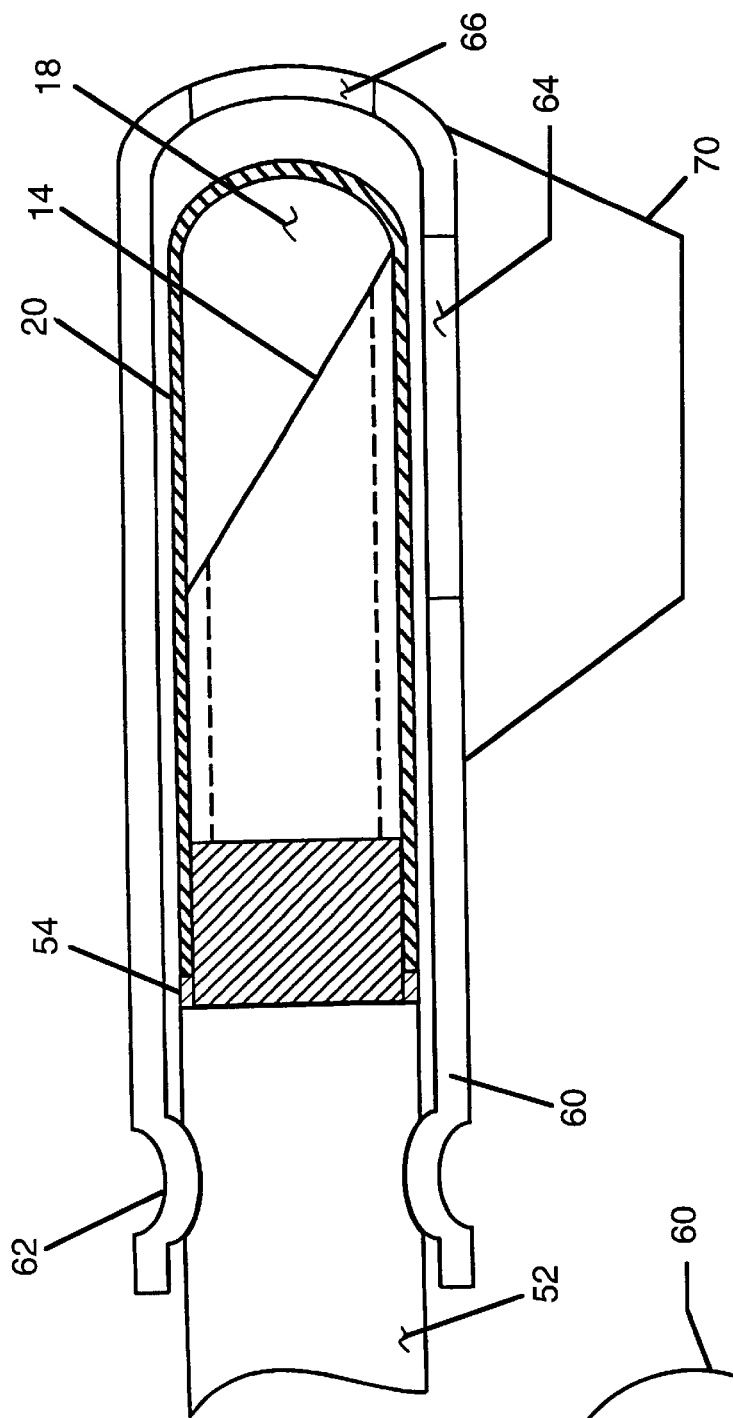
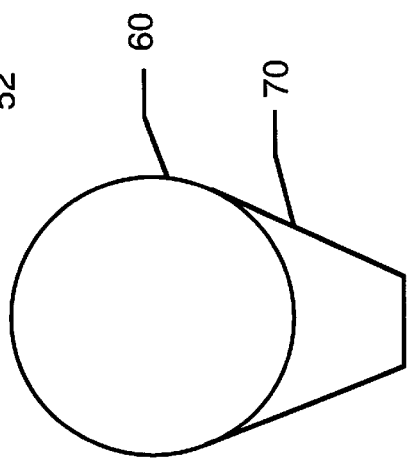
FIGURE 12a
FIGURE 12b

SIDE FIRING FIBER OPTIC LASER PROBE

This is a continuation of application No. 08/427,173 filed on Apr. 24, 1995. Now abandoned.

TECHNICAL FIELD

The subject invention relates to a fiber optic probe used to deliver laser radiation during a surgical procedure. The fiber optic probe is of the side firing type wherein light exits the fiber transverse to the longitudinal axis thereof.

BACKGROUND OF THE INVENTION

In the last decade, there has been a considerable increase in the use of lasers in surgery. Flexible optical fibers are often used to deliver laser light from a laser device to a treatment site. The delivery end of the fiber is typically encased in a metal sheathed probe having a design which is optimized for a particular procedure.

One example of a prior art probe can be found in U.S. Pat. No. 5,257,989, assigned to the same assignee herein and incorporated by reference. The probe described in this patent is used in various types of orthopedic applications. In this probe, the laser treatment beam emerges from the delivery end of the fiber and travels substantially parallel to the longitudinal axis thereof.

In many surgical applications, it is desirable to direct the exiting treatment beam along an axis transverse to the longitudinal axis of the fiber. In this manner, tissue which is alongside the probe can be treated.

In the prior art, there have been developed a wide variety of probes which are capable of directing an exiting treatment beam transverse to the longitudinal axis of the fiber. These types of probes typically include an angled element formed at the delivery end of the fiber. In one class of probes, the angled element is provided with a reflective coating. In another approach, the angled end element is oriented in a manner to cause the treatment beam to be totally internally reflected and redirected out of the side surface of the fiber.

In order to readily obtain total internal reflection at the angled end face of the fiber, there needs to be a significant difference between the index of refraction of the material forming the fiber and the index of refraction of the medium in which the fiber is situated. Total internal reflection is relatively easy to achieve when a conventional silica fiber is used in a gaseous environment. Some complexities are encountered, however, if the fiber is used in a liquid medium. In the latter case, the index of refraction of a typical biocompatible liquid medium (such as saline) is much closer to the index of refraction of a conventional silica fiber. Since the indices of refraction are quite similar, it is not possible to select a suitable angle for the reflecting end face which will redirect a large portion of the beam in the desired lateral direction.

One approach for overcoming this problem is to sealingly mount a transparent glass capillary over the delivery end of the fiber. The capillary is mounted in a manner to create an air pocket adjacent the angled face. This air pocket defines a medium adjacent the delivery end of the fiber which has an index of refraction sufficiently different from the index of refraction of the optical fiber that total internal reflection can take place at the angled face. By this arrangement, the angled face can be used to laterally redirect the treatment beam out of the side surface of the fiber. An example of the latter structure can be found in U.S. Pat. No. 4,740,047, issued Apr. 26, 1988, to Abe.

The use of a glass capillary surrounding the delivery end of a probe is effective to allow total internal reflection of light at an angled face when the fiber is used in a liquid medium. Unfortunately, some problems have arisen when such side firing probes have been used to delivery high energy pulses which are highly absorbed in the liquid medium. This situation is now being confronted in the latest generation of surgical lasers which generate more than 30 watts of laser energy at wavelengths in the two to three micron range. A high energy pulse generated at these wavelengths has a short penetration depth in the liquid medium and tends to super heat the fluid causing a vapor bubble to be created. This vapor bubble begins to form in a time period as short as 15 microseconds and then rapidly expands. At the end of the laser pulse (typically in the 350 microsecond range), the vapor bubble will rapidly collapse. As the bubble collapses, the implosion of the bubble creates high intensity shock waves or high velocity fluid jets which erode the capillary or fiber. This erosion can weaken or crack the capillary, often leading to catastrophic destruction in a short period of time. In another failure mode, the cavitation effects can also rupture the connection between the capillary and the fiber.

Accordingly, it would be desirable to provide an improved fiber optic probe having a glass capillary to permit side firing in a liquid medium and further including a means for shielding the glass capillary against destructive cavitation effects.

In most surgical procedures requiring a side firing probe, it is desirable that almost all of the light be transmitted out of the side surface of the fiber in the intended transverse direction. In practice, it has been found that a significant percentage of the light actually emerges from the fiber at undesired and unintended locations. In the case of a totally internally reflecting probe, the light leakage is primarily through the angled face. Where a reflecting coating is placed on the angled face, the light leakage will occur through other side surfaces of the fiber.

This problem of unintended light leakage from the fiber was discussed in the Abe patent, cited above. Abe attributed this problem to two different effects. First, Abe believed that light redirected by the angled face was once again re-reflected by the inner surface of the outer glass capillary. Abe also believed that a certain percentage of light initially struck the reflecting face at an angle less than would be necessary for total internal reflection and therefore would be transmitted through the angled face. In order to reduce the amount of light which leaks out of the delivery end of the fiber in a direction other than the desired side surface, Abe suggested providing a reflective coating on the surface of the capillary adjacent to the angled face of the fiber such that light leaking from the angled face would be redirected along the desired path. In addition, Abe suggested providing an antireflection coating on the surface of the capillary adjacent the side of the fiber through which the treatment beam is transmitted in order to minimize back reflections off the capillary.

While the use of an antireflection coating may actually function to reduce unwanted reflection of light, it can add significantly to the cost and complexity of the device. For example, it would be very difficult to design and apply an antireflection coating on the curved surface of either the capillary or the fiber. It is also believed that by proper selection of the angle of the reflecting face, all of the light initially striking the angled face can be redirected by total internal reflection and will not directly leak out of the end face as suggested by Abe. However, even if the angle of the reflecting face is properly chosen to achieve total internal reflection, light will still leak out of the fiber. Contrary to Abe's analysis, the inventors herein have found that a large portion of the light which is observed to leak out of the end face of the fiber is a result of secondary reflections of some of the light which has been totally internally reflected by the angled face. These secondary reflections can result in ten percent or more of total light traveling down the fiber being lost to leakage. It is an object of the subject invention to reduce these secondary reflections and the associated power loss.

It should be noted that in addition to the secondary reflections mentioned above, a small percentage of light is also lost through leakage due to Fresnel reflections at the various boundary surfaces. The subject invention is primarily directed to reducing or eliminating losses due to secondary reflections. The relatively smaller losses caused by Fresnel reflections at the surface boundaries can be reduced, if desired, with antireflection coatings.

The origin of the secondary reflections which are the primary focus of the present invention are discussed with reference to FIGS. 1, 2a and 2b. FIG. 1 is a cross-sectional view of the delivery end of an optical fiber 10. Various rays 12 of the treatment beam are shown striking the angled end face 14 of the fiber. As is well known, if the angle of incidence of these rays is greater than a critical angle, the rays will not travel through the end face 14 but will be totally internally reflected. In order to insure that all rays travelling down the fiber are totally internally reflected at the end face, the angle β of the end face must be correctly selected.

This angle β can be readily determined if the indices of refraction of the fiber and the medium surrounding the fiber are known. The approach for determining this angle β begins with a determination of the angle of incidence α of a ray (with respect to the surface normal of end face 14) which must be met or exceeded to produce total internal reflection. The angle of total internal reflection (TIR) may be calculated using the following formula:

$$\alpha(\text{TIR angle}) = \sin^{-1}(n_2/n_1) \quad \quad 1)$$

where $n_1$ is the index of refraction of the fiber core 16 and $n_2$ is the index of refraction of the medium 18 surrounding the fiber. In the case of a fiber used in a liquid medium, a transparent capillary 20 is provided to create an air pocket adjacent the end face to increase the difference in indices of refraction between the fiber core and the medium surrounding the fiber.

The next step in the process is to determine the maximum angle θ along which rays will propagate within the fiber. While a portion of the rays will propagate close to the central axis of the fiber, a significant portion of the energy will be guided off the walls of the fiber. The angle of maximum propagation θ is a function of the relative indices of refraction of the fiber core and the surrounding medium (cladding) as well as the intrinsic numerical aperture (NA) of the fiber and is given by the following formula:

$$\theta = \sin^{-1}[(n_1/n_2) \sin\tan^{-1}(\text{NA}_{fiber})] \quad \quad 2)$$

The selection of the angle β for the end surface is then made so that any rays propagating at the maximum angle θ with respect to the axis of the fiber will equal or exceed the TIR angle (α) when striking the end surface. All rays propagating along the fiber at less than the maximum propagation angle will exceed the TIR with respect to the end surface. Based on simple geometric principles, angle β is then given by:

$$\beta = 90 - \alpha - \theta \quad \quad 3)$$

Using empirical methods, it has been determined that the angle β can be set in the range of 37 to 38 degrees to produce total internal reflection of a treatment beam having a wavelength of 2.1 microns travelling down a fiber having a silica core and a silica cladding, a numerical aperture of 0.22 and wherein air is trapped in the capillary 20 adjacent the reflecting face. In practice, the assignee herein has manufactured probes wherein the angle β is on the order of 31 degrees. The shallower angle was selected in order to direct the exiting light in a more forward direction.

As noted above, by proper selection of the angle β, all of the light travelling down the fiber can be totally internally reflected when first striking the angled face. Therefore, it is believed that the secondary reflections which occur after the light has been reflected from the angled face are the actual cause of the majority of unwanted light leakage from the fiber. More specifically, after the rays 12 have been totally internally reflected, they are redirected down to the side surface 24 of the fiber. The majority of the light redirected in this fashion is transmitted through the side surface 24. However, a significant percentage of the light is also reflected back from the side surface. These secondary reflections can be seen in FIGS. 2a and 2b.

FIGS. 2a and 2b is a simplified end view of the delivery end of the fiber wherein the light is travelling towards the reader. For ease of analysis, the rays illustrated in these Figures are limited to those which propagate vertically downwardly after reflection from the end face. The additional issues which must be considered in analyzing the light having a horizontal propagation component are set forth below. With respect to the vertically propagating rays shown in FIG. 2a and 2b, it will be seen that the rays striking the side surface in a central region of the fiber (bounded by vertical lines T—T) are transmitted through the side surface 24. However, rays which strike the outer lobes 30 of the side surface are not transmitted but are reflected. The reason why some of the rays are transmitted while other rays are reflected is that the angle at which the rays strike the side surface of the fiber differs and is a function of the location where the rays strike the side surface.

For example, the rays which strike the side surface at the center point (C) form an angle of incidence of zero degrees. Due to the curved surface of the fiber, the angle of incidence of the rays striking the side surface increases as the position of the incident ray moves towards the outer lobes 30. For all rays striking the center region (between T—T), the angle of incidence remains below the angle necessary to cause total internal reflection and therefore are transmitted through the side surface. However, for rays which strike the side surface in the outer lobes 30, the angle of incidence exceeds the critical angle and the rays will be totally internally reflected. This light which is totally internally reflected is redirected in a helical manner back towards the angled face. A large portion of this re-reflected light will strike the angled face at an angle less than the critical angle and therefore be transmitted through the angled face. It is believed that the transmission of light due to these secondary reflections in the outer lobes 30 of the side surface 24 is primarily responsible for the unwanted light leaking out of the fiber and far outweighs the level of light lost due to conventional Fresnel reflections at the boundary surfaces. Accordingly, if these secondary reflections can be minimized, light leakage can be substantially reduced.

The analysis of the rays illustrated in FIGS. 2a and 2b was limited to light propagating directly downwardly after striking the angled face. In practice, the propagation direction of most light rays will also include a horizontal component. However, it is believed that in terms of the analysis of the percentage of light leaking out of the fiber due to secondary reflections, the effects of the horizontal component in the light propagation direction are minimal.

When the horizontal component of propagation is considered, it will be seen that some of the light will strike the side surface in the outer lobes 30 at less than the critical angle and will therefore be transmitted. On the other hand, some of the light having a horizontal propagation component striking the central region of the side surface of the fiber will have an angle of incidence greater than the critical angle and will therefore be totally internally reflected. This light will be redirected in a helical manner and be transmitted out of the angled face. It is believed that the light which is transmitted out of the side lobes (due to a horizontal propagation component) will be roughly equal to the amount of light which will be reflected by total internal reflection in the central region of the fiber (due to a horizontal propagation component) and therefore the simplified analysis contained herein limited to downwardly propagating light is reasonable and useful.

SUMMARY OF THE INVENTION

In accordance with the subject invention, a fiber optic probe is provided having an input end and a delivery end. The delivery end is provided with a angled end face configured to reflect light travelling down the fiber in a direction transverse to the longitudinal axis thereof. In the preferred embodiment, the angled face is configured to create total internal reflection.

In accordance with the subject invention, the probe is further provided with a means for reducing secondary reflections of light that has been initially reflected at the angled face and increasing the transmission of this light through the side surface of the fiber. This means is defined by configuring the delivery end of the probe to minimize the secondary reflections which occur at the fiber surface. This result is achieved by controlling the shape of the side surface of the fiber so that a higher percentage of the rays reflected off the angled face will be transmitted rather than internally reflected at the side surface of the fiber.

There are a number of approaches available which could be implemented in order to control the effective angle of incidence of light reaching the side surface of the fiber. In a relatively simple approach, the ratio of the diameters of the fiber cladding to the core can be increased thereby placing an upper limit on the angle of incidence of the rays of the treatment beam striking the side surface of the fiber. In another approach, the actual geometry of the cladding can be changed in the region of the side surface. This approach has the added benefit of allowing the designer to control the focal power of the interface. In this manner, the exiting treatment beam could be caused to diverge or be brought into a focus. The concept of using different cladding geometries to control the divergence of the treatment beam can be used independently and is viewed as a separate inventive development.

Another alternative approach to reducing secondary reflections is specifically related to the side firing probes which utilize a glass capillary for operation in a liquid medium. In this type of probe, the surface of the capillary can be optically fused in this region to the side surface of the fiber where light is to be transmitted. By optically fusing the capillary in this region, the effective cladding diameter is increased, thereby decreasing the angle of incidence and reducing secondary reflections. Optically fusing the capillary also eliminates two of the glass surface boundaries such that Fresnel losses are also reduced. In addition, in the case where the probe is used in a liquid medium and no vapor bubble is formed (i.e. at lower power levels or different wavelengths), the indices of the glass material forming the capillary and the outside liquid medium are relatively similar thereby increasing the critical angle and further minimizing total internal reflection at the side surface.

In a second aspect of the subject invention, a shield is provided for protecting the glass capillary from destruction by cavitation forces. The shield is rigid and self-supporting and preferably formed from a metal such as stainless steel. The shield functions to protect the glass capillary from the shock waves created when the vapor bubble in the liquid medium collapses, thereby substantially increasing the lifetime of the probe.

Further objects and advantages of the subject invention will become apparent from the following detailed description taken in conjunction with the drawings, in which:

BRIEF DESCRIPTION OF THE DRAWINGS

FIG. 1 a cross-sectional view of the delivery end of an optical fiber.

FIG. 2*a* is an end view of the delivery end of the optical fiber of FIG. 1.

FIG. 8*a* is a cross-sectional view of a sixth embodiment of the fiber optic probe of the subject invention.

FIG. 8*b* As a cross-sectional view of a fiber optic probe taken along the line 8*b* of FIG. 8*a*.

FIG. 11 is a cross-sectional view of a fiber optic probe including a support shield for protecting a glass capillary formed in accordance with the subject invention.

FIG. 12*a* is a cross-sectional view of an alternate configuration of a support shield.

FIG. 12*b* is an end view of the alternative configuration of the support shield in FIG. 12*a*.

FIG. 16b is a cross-sectional view of an alternate embodiment to the probe illustrated in FIG. 16a.

DETAILED DESCRIPTION OF THE PREFERRED EMBODIMENTS

Figure 2B:
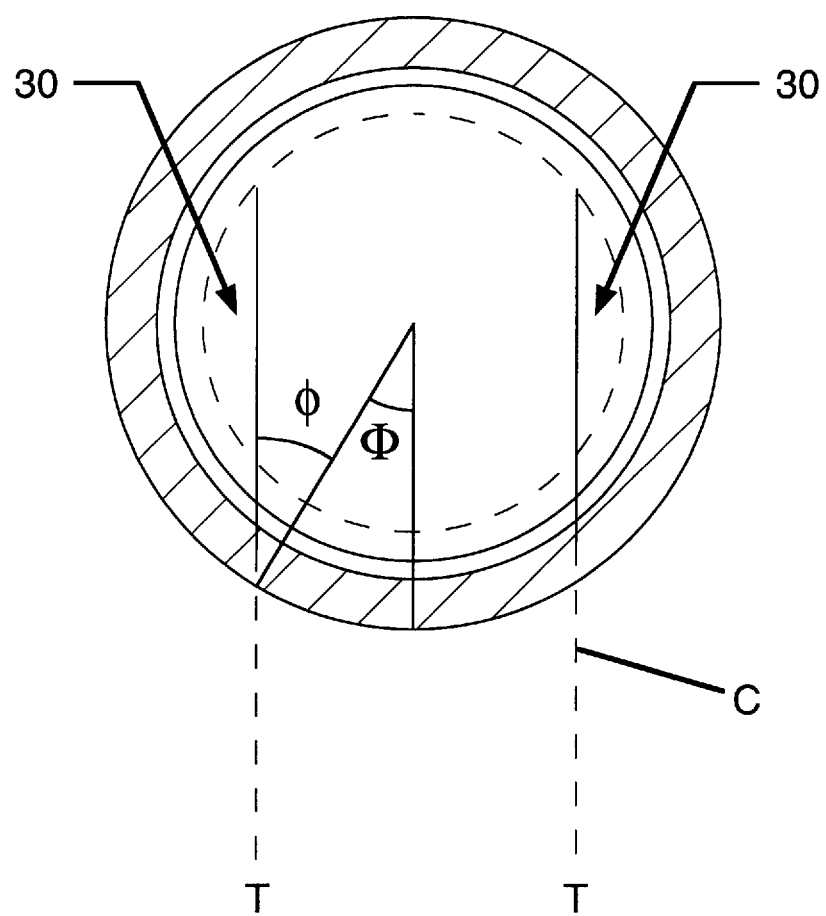
FIG. 2*b* is an end view of the delivery end of the optical fiber of FIG. 1 illustrating the angle where total internal reflections begin.

In a first aspect of the subject invention, secondary reflections which occur due to total internal reflection at the side surface of the probe are minimized to increase transmission in the desired direction. As illustrated in FIGS. 2a and 2b, these secondary reflections primarily occur in the outer lobes 30 of the fiber. The extent of the region where this effect occurs depends on the indices of refraction of the fiber and the surrounding material and the ratio between the diameters of the clad and the core.

Given the indices of refraction of the fiber and of the surrounding air, and using formula (1) above, the angle of incidence $\phi$ on the fiber/air surface where total internal reflections begin for downwardly propagating light can be determined as follows:

$$\phi = \sin^{-1}(n_{air}/n_{fiber})$$

$$\phi = \sin^{-1}(1.00/1.4)$$

$$\phi \approx 46 \text{ degrees}$$

Therefore, for a conventional fiber, any downwardly propagating light striking the side surface from the bottom center (point C of FIG. 2a) though an arc $\Phi$ (as shown in FIG. 2b), where $\Phi$ is less than 90°–$\phi$ (44 degrees) on either side thereof, will be transmitted through that surface. However, any downwardly propagating light which strikes the side surface beyond 44 degrees from the center point (and out to 90 degrees) will be totally internally reflected. Therefore, it is in these outer lobes that the side surface must be modified in order to reduce secondary reflections. As noted above, due to the presence of a horizontal component in the direction of propagation of light, some of the rays striking the side surface in the side lobes will be transmitted while some of the rays striking the side surface in the center region will be reflected.

Figure 3B:
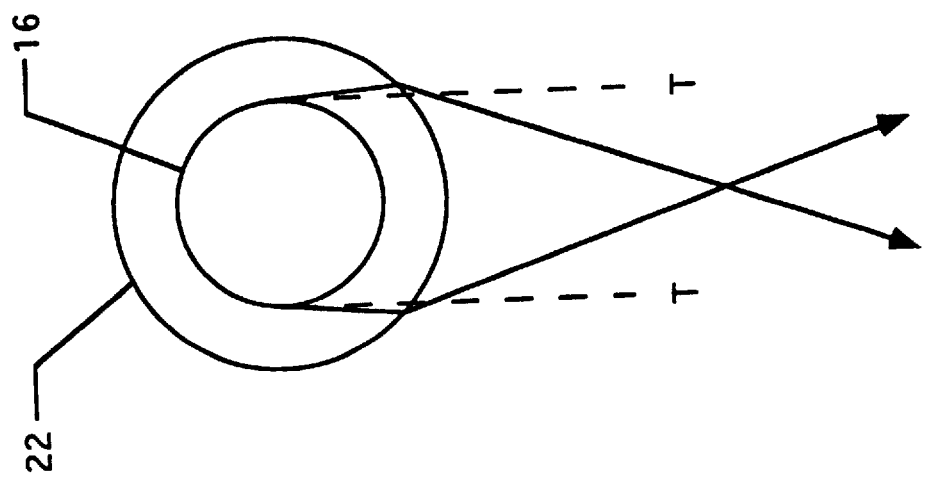
FIG. 3*b* is an end view of the probe of FIG. 3*a*.
Figure 3A:
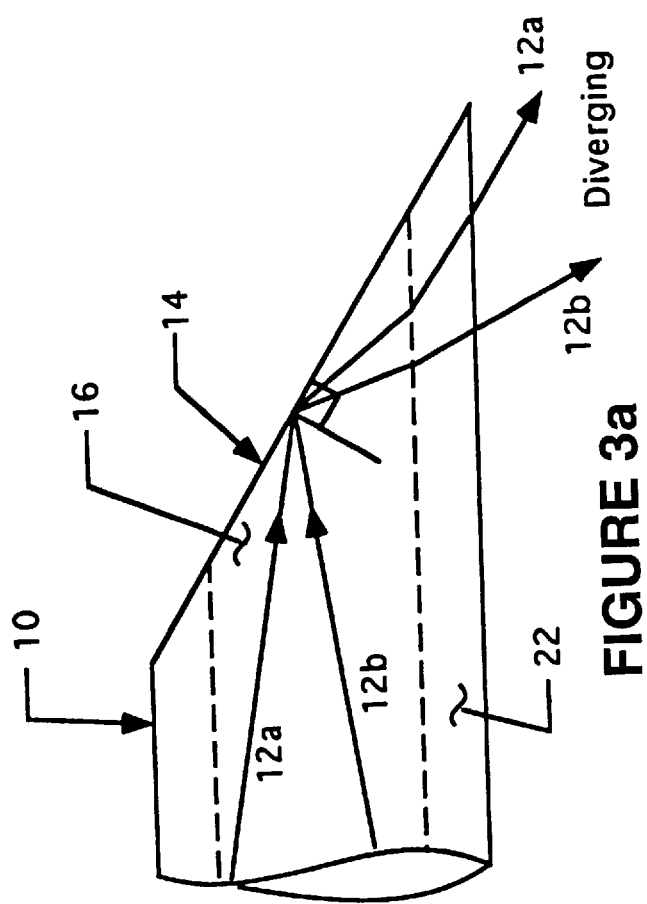
FIG. 3*a* is a side view of a fiber optic probe including a configuration for reducing secondary reflections in accordance with the subject invention.

FIGS. 3a and 3b illustrate a first embodiment for achieving this goal. In this embodiment, the ratio of the diameters between the fiber cladding to the fiber core is increased. In a conventional fiber, this ratio is typically in the range of 1.1 to 1.2. In accordance with the subject invention, this ratio is increased to at least 1.3 and preferably in excess of 1.4. This ratio can be achieved by using a conventional core diameter and increasing the clad diameter. Conversely, the standard clad diameter could be maintained will reducing the diameter of the core. One skilled in the art could also modify both the standard core and clad diameters to balance transmission characteristics with the total size of the fiber.

The effect of increasing the clad to core ratio is to minimize the amount of light reflected off the angled face 14 that will strike the surface of the cladding beyond the 44 degree total internal reflection boundary calculated above. In this manner, a much higher percentage of the light passing out of the core will be transmitted at the clad/air interface and secondary reflections are reduced. The following data represents an analysis of light leaking out of a conventional fiber due to secondary reflections having a 550 micron core and varying clad diameters (in microns).

| Clad Diameter | Clad-Core Ratio | % Light Loss |
|---|---|---|
| 600 | 1.1 (standard) | 13.64 |
| 660 | 1.2 | 7.82 |
| 715 | 1.3 | 3.47 |
| 770 | 1.4 | 0.24 |
| 790 | 1.43 | ≈0.00 |

As can be seen, significant improvements can be achieved with only modest variations in the ratio of the core to clad diameters.

As illustrated in FIG. 3a, light emerging from the fiber along the longitudinal axis is diverging. Conversely, light emerging transverse to the fiber axis is focused as illustrated in FIG. 3b. The light transmission patterns can be modified by varying the configuration of the cladding as discussed below with respect to FIGS. 4 to 7.

Figure 4:
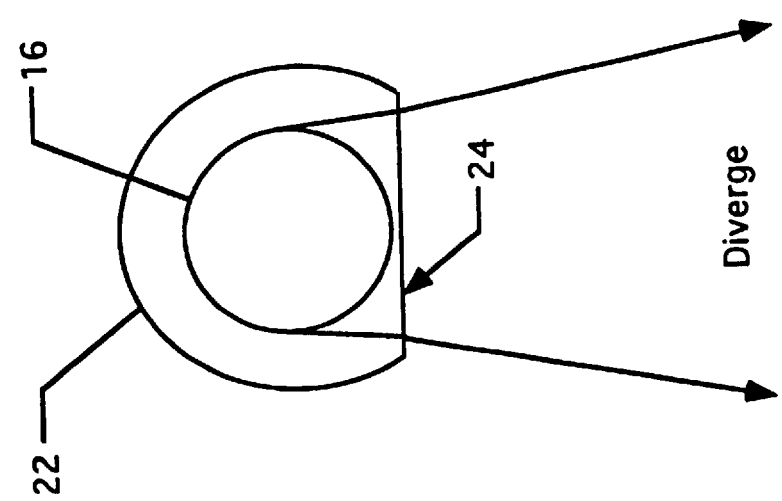
FIG. 4 is a view similar to FIG. 3*b* of a second embodiment of the fiber optic probe of the subject invention.

FIG. 4 illustrates an embodiment where the outer side surface of the cladding has a first radius of curvature. In the transmission region, the outer side cladding has a second radius of curvature that differs from the first radius of curvature. The cladding of the transmission region is provided with a generally planar configuration. Using this configuration, all of the rays which are reflected from the angled end face of the fiber intersect with the side surface of the cladding at approximately ninety degrees and therefore would be transmitted. The configuration of the cladding in FIG. 4 would function to cause the light to diverge in the axis transverse to the axis of the fiber.

Figure 5:
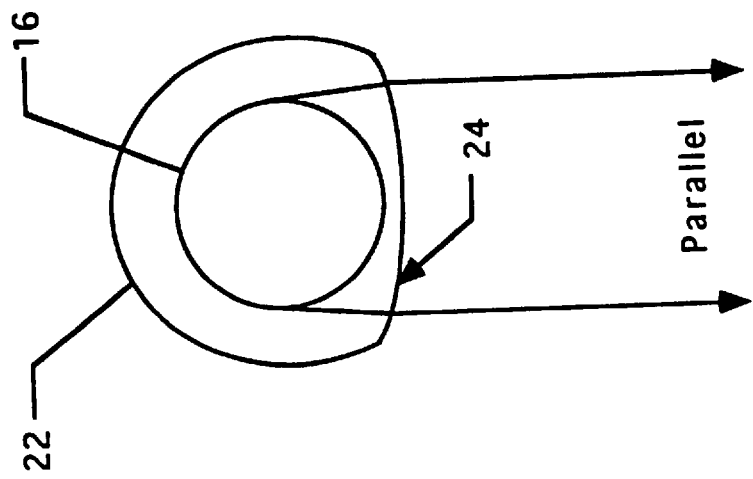
FIG. 5 is a view similar to FIG. 3*b* of a third embodiment of the fiber optic probe of the subject invention.

FIG. 5 illustrates an embodiment where the outer side surface 24 of the cladding has a first radius of curvature. In the transmission region, the outer side cladding has a second radius of curvature that differs from the first radius of curvature. In the transmission region illustrated in FIG. 5, the cladding is provided with a concave configuration. Once again this configuration will substantially eliminate secondary reflections from the side surface by keeping the angle of incidence of rays striking the clad/air interface below the critical angle for total internal reflection. In addition, the concave curvature of the cladding will allow for further variations in the pattern of transmitted light. Such light can be controlled to diverge, converge or to be substantially collimated in the axis transverse to the fiber axis.

Figure 7:
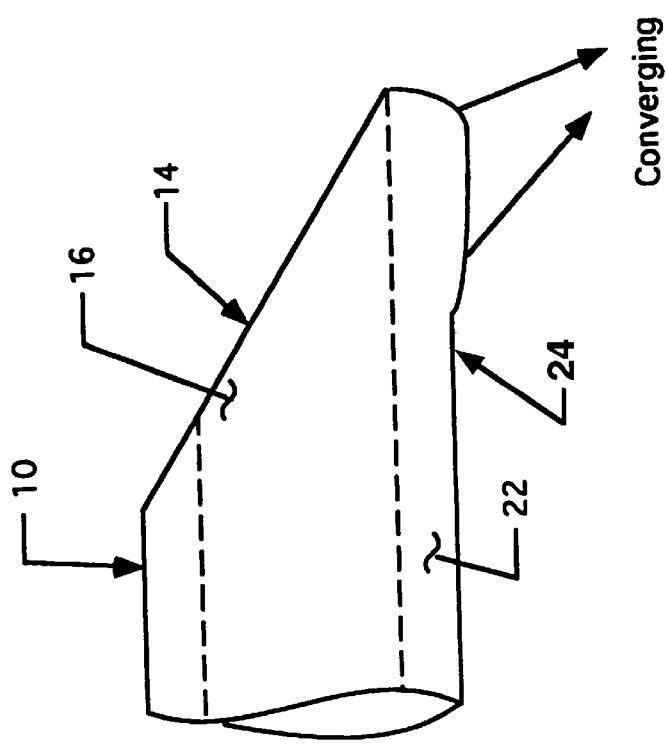
FIG. 7 is a view similar to FIG. 3*a* of a fifth embodiment of the fiber optic probe of the subject invention.
Figure 6:
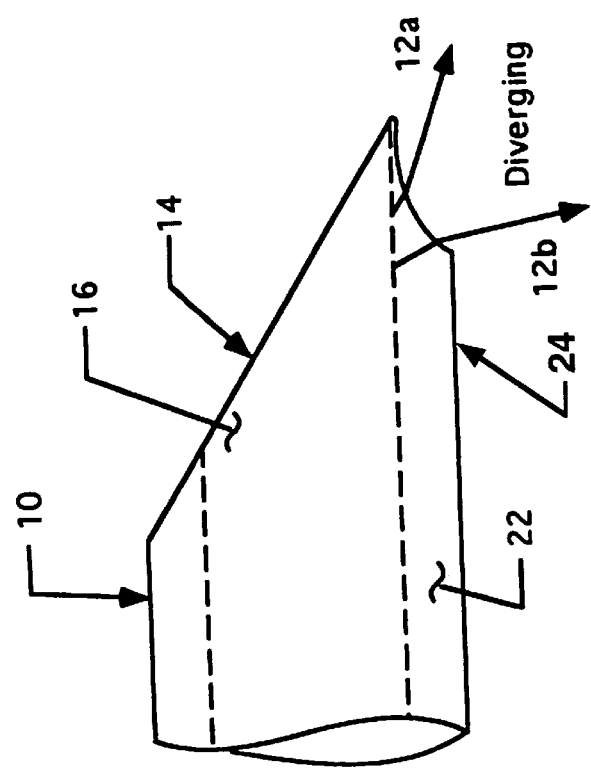
FIG. 6 is a view similar to FIG. 3*a* of a fourth embodiment of the fiber optic probe of the subject invention.

FIGS. 6 and 7 illustrate approaches for modifying the light exiting the fiber along its longitudinal axis. These configurations could be combined with the configurations shown above. In FIG. 6, the side surface 24 of the cladding 22 is formed with a concave configuration extending along the fiber axis which functions to increase the divergence of the treatment beam in this axis. In FIG. 7, the side surface 24 of the cladding 22 is formed with a convex configuration to focus the light rays in the fiber axis.

It should be noted that even if secondary reflections were not a problem, the use of claddings having non-convex geometries (i.e. planar and concave) to control the divergence of light could be independently beneficial.

FIGS. 8a and 8b illustrate an approach particularly suited for fiber optic probes that include a glass capillary to facilitate side firing in a liquid medium. As seen in FIGS. 8a and 8b, a conventional optical fiber 10 is provided with an angled reflecting face 14. At least a portion of the transparent capillary 20 is sealed to the fiber so that an air pocket 18 is trapped adjacent the reflecting face. By this arrangement, total internal reflection at the angled face is facilitated even if the probe is immersed in a liquid medium.

In the prior designs of optical probes using glass capillaries, the rear region of the capillary would be sealed to the fiber using a conventional adhesive. As noted in the patent to Abe, in the region near the delivery end of the probe, a small air gap occurs between the inner surface of the capillary and the outer surface of the fiber. Abe suggests that reflections off the capillary surface might be eliminated if the manufacturing tolerances could be increased to obtain a tight fit between the elements thereby eliminating the air gap. However, Abe correctly rejects this approach as not being suitable for mass production. Abe's chosen solution, which does not prevent these reflections but instead redirects them in an unspecified direction, includes depositing a reflective coating on the opposite outside surface of the capillary and depositing an anti-reflective coating on the outside surface of the output side of the capillary.

The inventors herein believe that the substantial enhancements in performance can be achieved using an alternative approach, wherein the capillary is optically coupled to the outer surface of the fiber. One method of achieving this goal is to fuse the capillary to the fiber. Such optical fusing can be achieved by melting the capillary with a localized heat source. In one experimental embodiment, a focused light beam from a carbon dioxide laser was used to melt and fuse a capillary to the side surface of a fiber. Another approach to achieve this optical coupling would be to fill the void between the outer surface of the fiber and the inner surface of the capillary with a transparent index matching material. A further approach would be to employ well known fritting techniques commonly used in the laser industry to bond various crystals and glasses. As indicated in FIGS. 8a and 8b, the region of optical coupling can be limited to the side surface 24 where light is redirected from the angled face of the fiber. As can be appreciated, a fiber optic probe would be easier to fabricate using either of the these latter approaches rather than by attempting to obtain a close fit through high mechanical tolerances as suggested by Abe.

Two distinct advantages can be obtained by optically coupling the capillary to the fiber. First, the Fresnel reflections off the inner surface of the fiber and the inside surface of the capillary will be eliminated. Since these reflections are relatively small, this improvement, while desirable, is not that significant. Of greater importance is the fact that by optically coupling the capillary to the fiber, secondary reflections are minimized. This result is achieved because the optical coupling of the capillary functions to increase the effective diameter of the cladding thereby increasing the cladding to core ratio. In this manner, the structure as shown in FIG. 8b will be optically equivalent to the structure shown in FIG. 3b.

Optically coupling the capillary to the fiber has an added benefit where the probe is used in a liquid medium and a vapor bubble is not formed by the laser energy. As noted above, in certain situations, such as when high power pulses from a Ho:YAG laser are used for treatment, a vapor bubble is formed outside the capillary. This vapor bubble has an index of refraction similar to air. However, the subject probe might also be used at lower power levels and/or with different wavelengths such as 1.06 microns (Nd:YAG) where no vapor bubble is formed.

In the case where no vapor bubble is formed, the liquid medium surrounds the fiber and the index of refraction of the liquid medium is relatively close to the index of refraction of the glass capillary. Since the indices of refraction at the glass/liquid interface are similar, the critical angle necessary for total internal reflection will be relatively high such that the problems of secondary reflections will be reduced with a capillary of only minimal thickness.

Figure 9:
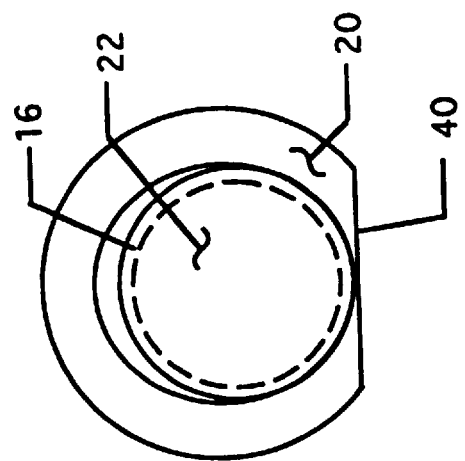
FIG. 9 a cross-sectional view of a seventh embodiment of a fiber optic probe of the subject invention.

FIG. 9 is a cross-sectional view of a fiber optic probe which combines the features of the embodiments shown in FIGS. 4 and 8. More specifically, the probe includes a central fiber having a conventional core 16 and clad 22. A capillary 20 is provided having one side thereof optically coupled to the side surface 24 of the fiber. In this embodiment, the outer side surface 40 of the capillary is formed with a planar configuration. By this arrangement, the effective clad geometry of the fiber in FIG. 9 can be made to be the optical equivalent of the clad geometry shown in FIG. 4.

Figure 10:
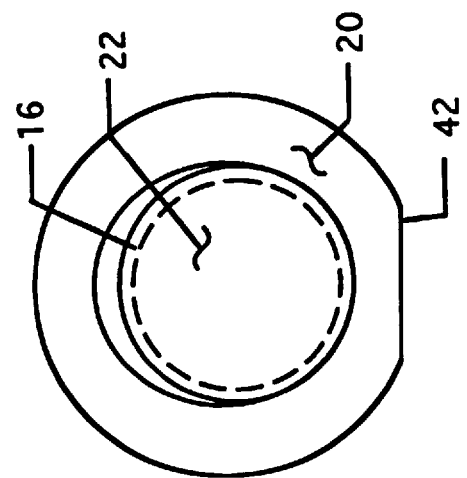
FIG. 10 is a cross-sectional view of a seventh embodiment of a fiber optic probe of the subject invention.

FIG. 10 is a cross-sectional view of a fiber optic probe which combines the features of the embodiments shown in FIGS. 5, 8a and 8b. As in the FIG. 9 embodiment, the probe includes a central fiber having a conventional core 16 and clad 22. A capillary is provided having one side thereof optically coupled to the side surface 24 of the fiber. In the embodiment of FIG. 10, the outer side surface 42 of the capillary is formed with a concave configuration. By this arrangement, the effective clad geometry of the fiber in FIG. 10 can be made to be the optical equivalent of the clad geometry shown in FIG. 5.

It should be noted that the concept of directly changing the clad geometry to reduce secondary reflections as shown in FIGS. 3 to 5 could be implemented in a fiber optic probe having a conventional sealed glass capillary. In the latter case, it would not be necessary to optically couple the capillary to the fiber in order to eliminate the secondary reflections in the fiber itself.

It should also be noted that the approaches described herein could be used to benefit side firing probes that utilize reflective coatings on the angled face 14 to create reflection of the treatment beam. In these devices, secondary reflections typically do not exit the fiber through the angled face but are re-reflected out through other parts of the fiber. By reducing secondary reflections, more light can be directed in the desired direction. Also, by optically coupling the secondary reflections out of the fiber, the optical power remaining in the fiber that can degrade the reflective coatings by being re-reflected out through other parts of the fiber is drastically reduced.

FIGS. 11 through 14 illustrate another aspect of the subject invention designed to increase the life of a fiber optic probe provided with a capillary to facilitate side firing in a liquid medium. FIG. 11 illustrates a fiber optic probe having a central optical fiber 10. The delivery end of the fiber is provided with an angled face 14. A portion of the buffer layer 50 is stripped away from the delivery end of the fiber.

A glass capillary 20 is mounted over the delivery end of the fiber. A flexible tube 52 is mounted around the fiber behind the capillary. An epoxy joint 54 is provided between the tube and the capillary after assembly for stress relief. An air pocket 18 is created adjacent the angled face 14 of the fiber. In accordance with the first aspect of the subject invention discussed above, the capillary can be optically coupled to the side surface 24 of the fiber to reduce secondary reflections.

In accordance with the second aspect of the subject invention, a tubular shield 60 is mounted about the capillary 20 and a portion of tube 52. The free end 62 of the shield is physically crimped against tube 52 to provide a secure mounting and to hold the capillary in place. Shield 60 is formed from a rigid, self supporting material. The shield can be formed from a biocompatible stainless steel (such as "316") having a thickness on the order of 4 to 5 thousandths of an inch. Shield 60 further includes an opening 64 aligned with the side surface of the fiber and defines an aperture through which light can be transmitted. The distal portion 66 of the shield can be open ended.

Shield 60 is provided to protect the fiber and the capillary from the destructive cavitation forces encountered when the probe is used to deliver high energy pulses which are highly absorbed in the liquid medium surrounding the probe. By extending the end 62 of the shield beyond the end of the capillary and over the tube 52, the capillary mounting is protected from the cantilever forces applied to the capillary during use. The breakage of the capillary to fiber connection is the most common form of probe failure. The cantilever forces which cause this breakage are the result of the shockwave action of the medium as well as the torque applied to the probe by the surgeon.

Using the design shown in FIG. 11, the resistance to destruction of the fiber has been dramatically improved. More specifically, prior art probes which did not include the subject shield would typically fail after being exposed to successive pulses which resulted in a cumulative exposure on the order of 50 to 120 kilojoules. In contrast, seven experimental probes, which were provided with the shield structure of FIG. 9, were each subjected to in excess of 700 kilojoules of cumulative energy and could not be made to fail.

FIGS. 12*a* and 12*b* illustrates a probe similar to FIG. 11 where the side surface 70 of the shield 60 is modified. In this embodiment, the side surface 70 is provided with a planar configuration designed to create a snow plow effect with respect to the cavitation shocks. In this manner, the cavitation shocks can be more efficiently directed away from the capillary and the fiber.

Figure 14:
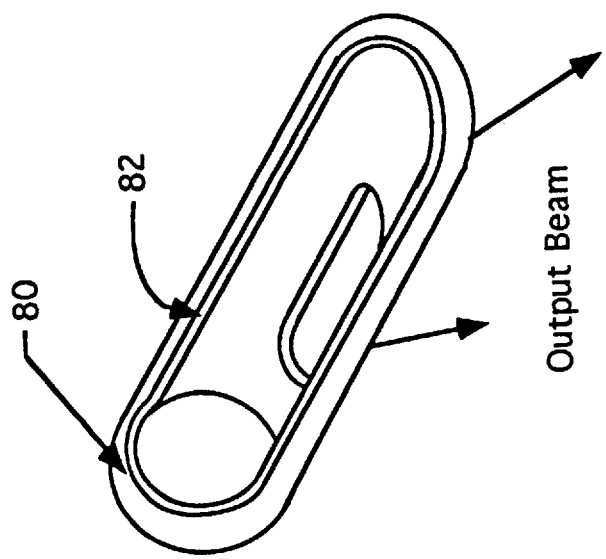
FIG. 14 is a further alternative configuration for a support shield.
Figure 13:
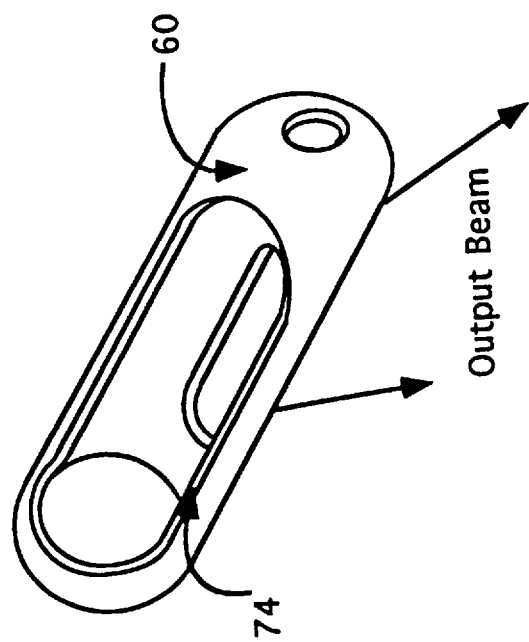
FIG. 13 is a perspective view of still another alternative configuration for a support shield.

FIGS. 13 and 14 are further alternate configurations for a shield 60. Both of these Figures are intended to illustrate that the critical region of protection is on the side surface of the probe where the light exits the fiber, since this is the region primarily exposed to the cavitation effects. Thus, the embodiment of FIG. 11 includes a large aperture 74 in the upper surface of the shield 60. This concept is extended in the embodiment of FIG. 14 where shield 60 includes a ring mount 80 and only a semi-cylindrical main body portion 82 for protecting against the cavitation effects.

Figure 15A:
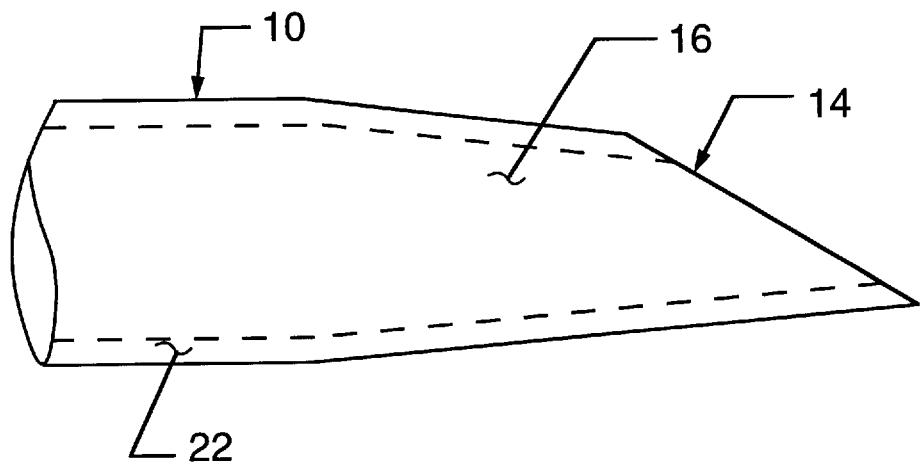
FIG. 15*a* is a cross-sectional view of the eighth embodiment of the fiber optic probe of the subject invention.
Figure 15B:
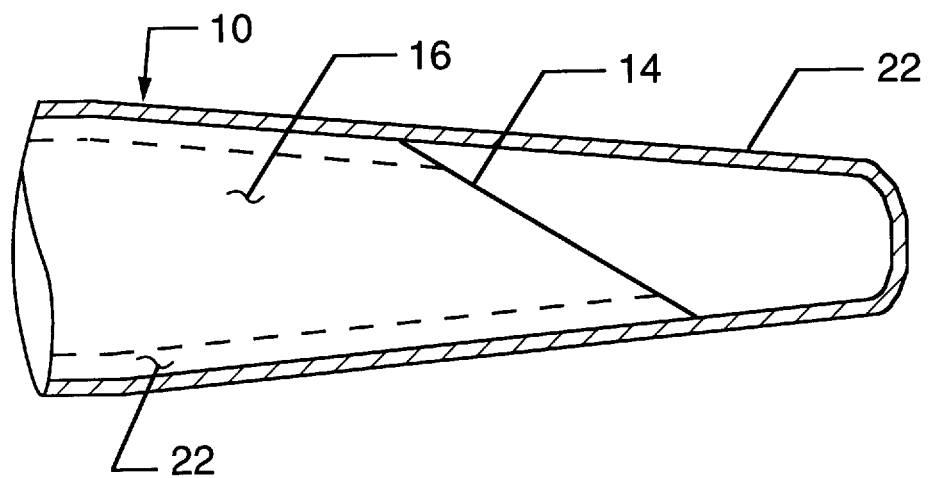
FIG. 15*b* is a cross-sectional view of the eighth embodiment of the present invention combined with a capillary.

FIGS. 15*a* and 15*b* illustrate another embodiment of the present invention. The optical fiber 10 in FIG. 15*a* terminates in a tapered delivery end, where both the core 16 and clad 22 are tapered near the reflective face 14. The optical fiber in FIG. 15*b* is the same, except the associated capillary 20 is also tapered at the delivery end. Tapering of the delivery end as shown in FIGS. 15*a* and 15*b* can be incorporated in any of the above described embodiments to manipulate the power density to produce better focusing and spot sizes of the laser energy outside the optical fiber.

Figure 16A:
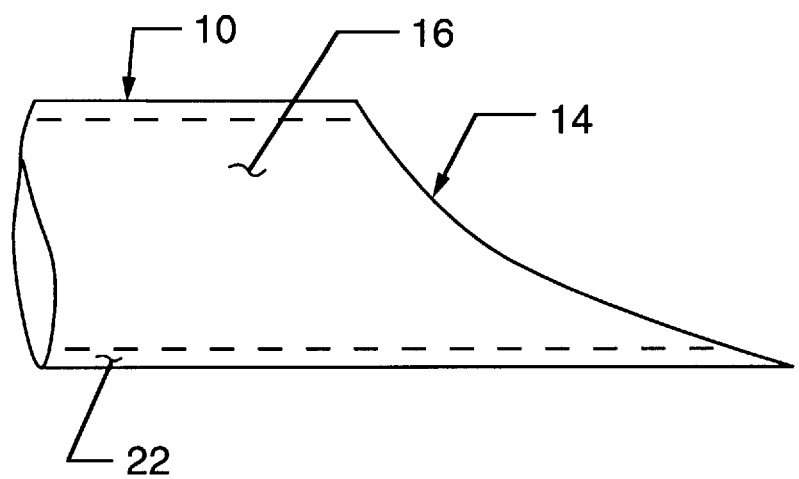
FIG. 16*a* is a cross-sectional view of the ninth embodiment of the present invention.
Figure 16B:
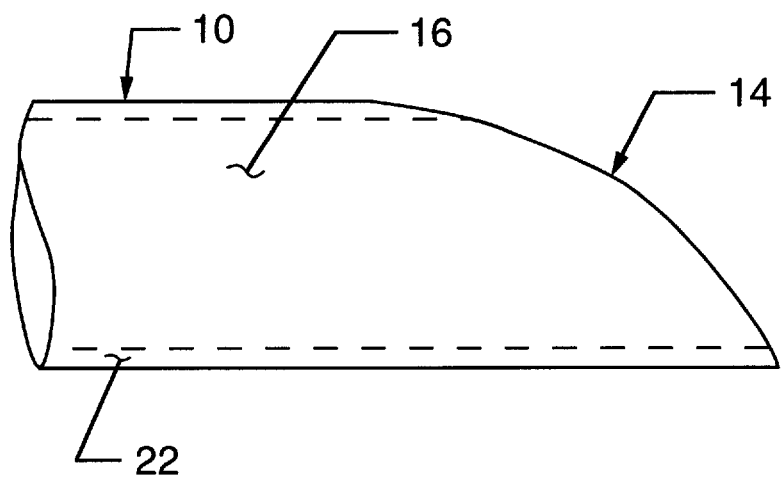

In a still another embodiment of the present invention, the reflective face 14 is non-planar to either increase or decrease the divergence of light reflected therefrom, as illustrated in FIGS. 16*a* and 16*b*. The concave and/or convex shape (FIGS. 16*a* and 16*b*, respectively) of the reflective surface 14 provides the desired focusing of the beam exiting the fiber. The reflective surface 14 can be non-planar in one axis in the plane of the reflecting face and planar in an orthogonal axis to the one axis, or can be non-planar in both axes.

In summary there has been disclosed a side firing fiber optic probe which includes an enhanced configuration designed to reduce secondary reflections which lead to unwanted light leakage and energy loss. The enhanced configuration can be defined by various actual or effective cladding geometries which can also be used to control the divergence of light exiting the fiber. In a further aspect of the invention, a rigid, self supporting shield structure has been described for increasing the lifetime of probes which are used to deliver a high energy treatment beam.

While the subject invention has been described with reference to the preferred embodiments, various changes and modifications could be made therein, by one skilled in the art, without varying from the scope and spirit of the subject invention as defined by the appended claims.

We claim:

1. A fiber optic probe for delivering laser light comprising:

an optical fiber having an input end and a delivery end, with the delivery end including a means for redirecting light travelling down the fiber in a direction transverse to a longitudinal axis of the fiber in a manner to exit the fiber through a side surface thereof; and said fiber includes a central core and an outer clad having a first radius of curvature, wherein a portion of the outer clad forming the side surface of the fiber is provided with a beam controlling surface to control at least one of divergence, convergence and collimation of the laser light passing through said side surface, said beam controlling surface having a second radius of curvature that is different than said first radius of curvature.

2. A probe as recited in claim 1 wherein the beam controlling surface is a planar surface.

3. A probe as recited in claim 1 wherein the beam controlling surface is a concave surface.

4. A probe as recited in claim 1 wherein the beam controlling surface is a convex surface.

5. A probe as recited in claim 1 wherein the delivery end of said optical fiber is tapered.

6. A probe as recited in claim 1 wherein:

the means for redirecting light is defined by a reflecting face disposed at a non-normal angle with respect to the longitudinal axis of the fiber to reflect the light travelling down the fiber by total internal reflection; and the probe further including a transparent capillary sealingly mounted to the delivery end of the fiber and being configured such that a portion of an inner surface of the capillary adjacent the reflecting face of the fiber is spaced therefrom to define an air space therebetween and wherein a portion of the inner surface of the capillary adjacent the side surface of the fiber is optically coupled thereto so that an amount of light which is totally internally reflected at the side surface is reduced.

7. A probe as recited in claim 6 wherein the reflecting face is non-planar to alter the divergence of the light reflected thereby.

8. A probe as recited in claim 7 wherein the reflecting face is non-planar in one axis in a plane of the reflecting face and planar in an orthogonal axis to the one axis.

9. A probe as recited in claim 6 wherein said capillary is fused to said side surface to define the optical coupling.

10. A probe as recited in claim 6 wherein a transparent index matching material is provided between the capillary and the side surface to create optical coupling therebetween.

11. A fiber optic probe for delivering laser light comprising:

an optical fiber having an input end and a delivery end, with the delivery end including a reflecting face disposed at a non-normal angle with respect to a longitudinal axis of the fiber in a manner so that light travelling down the fiber will be reflected at the face and redirected in a direction transverse to the longitudinal axis of the fiber in a manner to exit the fiber through a side surface thereof; and said fiber includes a central core and an outer clad having a first radius of curvature, wherein a portion of the outer clad forming the side surface of the fiber is provided with a beam controlling surface to control at least one of divergence, convergence and collimation of the laser light passing through said side surface, said beam controlling surface having a second radius of curvature that is different than said first radius of curvature.

12. A probe as recited in claim 11 wherein the beam controlling surface is a planar surface.

13. A probe as recited in claim 11 wherein the beam controlling surface is a concave surface.

14. A probe as recited in claim 11 wherein the beam controlling surface is a convex surface.

15. A probe as recited in claim 11 wherein:
the reflecting face is disposed to reflect the light travelling down the fiber by total internal reflection; and
said probe further including a transparent capillary sealingly mounted to the delivery end of the fiber and being configured such that a portion of an inner surface of the capillary adjacent the reflecting face of the fiber is spaced therefrom to define an air space therebetween and wherein a portion of the inner surface of the capillary adjacent the side surface of the fiber is optically coupled thereto so that an amount of light which is totally internally reflected at the side surface is reduced.

16. A probe as recited in claim 15 wherein said capillary is fused to said side surface to define the optical coupling.

17. A fiber optic probe for delivering laser light comprising:
an optical fiber having an input end and a delivery end, with the delivery end including a reflecting face disposed at a non-normal angle with respect to the longitudinal axis of the fiber;
a transparent capillary surrounding the delivery end of the fiber and creating an air pocket adjacent the reflecting face of the fiber so that light travelling down the fiber will be totally internally reflected at the angled face and redirected in a direction transverse to a longitudinal axis of the fiber in a manner to exit the fiber through a side surface thereof; and
a rigid, self-supporting, shield mounted to said fiber and surrounding at least a portion of the capillary along the side surface of the fiber, said shield including an opening to permit the transmission of light therethrough, said shield functioning to protect the capillary against destructive shockwave forces during use.

18. A probe as recited in claim 17 wherein said shield extends along a length of the fiber away from said reflecting face and beyond an end of the capillary in a manner to limit flexing of the fiber in a region adjacent the end of the capillary.

19. A probe as recited in claim 17 wherein said shield is formed from metal.

20. A probe as recited in claim 17 wherein said shield is formed from stainless steel.

21. A probe as recited in claim 17 further including a tubular member surrounding said fiber and adjacent an end of the capillary and wherein said shield extends over a portion of said tubular member as is connected thereto.

22. A fiber optic probe for delivering light comprising:
an elongated core for transmitting light, said core having an input end and a delivery end;
a clad surrounding the core;
means located at the delivery end of the core for redirecting the light travelling down the core in a direction transverse to a longitudinal axis of the core in a manner to exit the core and clad through side surfaces thereof, and wherein an outer surface of the clad in a region of said side surface including a non-convex curvature to alter a propagation path of the light transmitted therethrough.

23. A probe as recited in claim 20 wherein the outer surface of the clad in a region of said side surface has a planar configuration.

24. A probe as recited in claim 20 wherein the outer surface of the clad in a region of said side surface has a concave configuration.

25. A probe as recited in claim 20 wherein the outer surface of the clad in a region of said side surface has a concave cylindrical configuration and where a longitudinal axis of the cylindrical configuration is parallel to the longitudinal axis of the core.

26. A probe as recited in claim 22 wherein the outer surface of the clad in a region of said side surface has a concave cylindrical configuration and where a longitudinal axis of the cylindrical configuration is perpendicular to the longitudinal axis of the core.

27. A probe as recited in claim 22 wherein the means for redirecting light is defined by a reflecting face disposed at a non-normal angle with respect to the longitudinal axis of the core and wherein the probe further includes a transparent capillary sealingly mounted to the delivery end of probe and being configured such that a portion of an inner surface of the capillary adjacent the reflecting face of the core is spaced therefrom to define an air space therebetween and wherein a portion of the inner surface of the capillary adjacent the side surface of the clad is optically coupled thereto such that the clad and capillary function together to define said non-convex curvature.

28. A probe as recited in claim 27 wherein an outer surface of the capillary in a region of said side surface has a planar configuration.

29. A probe as recited in claim 27 wherein an outer surface of the capillary in a region of said side surface has a concave configuration.

30. A fiber optic probe for delivering laser light comprising:
an optical fiber having an input end and a delivery end, with the delivery end including a reflecting face disposed at a non-normal angle with respect to a longitudinal axis of the fiber in a manner so that light travelling down the fiber will be reflected at the face and redirected in a direction transverse to the longitudinal axis of the fiber in a manner to exit the fiber through a side surface thereof, said reflecting face is non-planar to alter at least one of divergence, convergence and collimation of the light reflected thereby.

31. A probe as recited in claim 30 wherein the reflecting face is non-planar in one axis in a plane of the reflecting face and planar in an orthogonal axis to the one axis.

32. A probe as recited in claim 30 further comprising:
a transparent capillary sealingly mounted to the delivery end of the fiber and being configured such that a portion of an inner surface of the capillary adjacent the reflecting face of the fiber is spaced therefrom to define an air space therebetween and wherein a portion of the inner surface of the capillary adjacent the side surface of the fiber is optically coupled thereto so that an amount of light which is totally internally reflected at the side surface is reduced.

* * * * *